(12) United States Patent
Provost et al.

(10) Patent No.: US 7,194,416 B1
(45) Date of Patent: Mar. 20, 2007

(54) INTERACTIVE CREATION AND ADJUDICATION OF HEALTH CARE INSURANCE CLAIMS

(75) Inventors: Wayne A. Provost, Salt Lake City, UT (US); Vaughn C. Cecil, Crossville, TN (US); John W. Kwant, Jr., Midvale, UT (US); Brian E. Peterson, Salt Lake City, UT (US)

(73) Assignee: P5, Inc., Salt Lake City, UT (US)

( * ) Notice: Subject to any disclaimer, the term of this patent is extended or adjusted under 35 U.S.C. 154(b) by 1097 days.

(21) Appl. No.: 09/724,097

(22) Filed: Nov. 28, 2000

Related U.S. Application Data (63) Continuation of application No. 09/204,886, filed on Dec. 3, 1998, now Pat. No. 6,341,265.

(51) Int. Cl.
*G06Q 40/00* (2006.01)
*G06Q 99/00* (2006.01)
(52) U.S. Cl. .................................... 705/4; 707/104.1
(58) Field of Classification Search .................... 705/2, 705/3, 4; 600/300, 301; 707/104.1
See application file for complete search history.

(56) References Cited

U.S. PATENT DOCUMENTS

| | | | | |
|---|---|---|---|---|
| 4,491,725 A | 1/1985 | Pritchard | .................... | 235/375 |
| 4,831,526 A | 5/1989 | Luchs et al. | ................ | 364/401 |
| 4,858,121 A | 8/1989 | Barber et al. | ............... | 364/406 |
| 5,225,976 A | 7/1993 | Tawil | ......................... | 364/401 |
| 5,235,507 A | 8/1993 | Sackler et al. | .............. | 364/401 |
| 5,253,164 A | 10/1993 | Holloway et al. | .......... | 364/406 |

(Continued)

FOREIGN PATENT DOCUMENTS

WO    WO 2001/09701 A    2/2001

OTHER PUBLICATIONS

Hagland, Mark Healtheon: Zigging and Zagging to adjust to health care realities, Health Management Technology; Atalnata; Jul. 1997 vol. 18, Issue 18, p. 30, cited in parent US patent 6,341,265.*

(Continued)

*Primary Examiner*—Sam Rimell
(74) *Attorney, Agent, or Firm*—Workman Nydegger (57) ABSTRACT

Methods and systems for interactively creating and submitting insurance claims and determining whether the submitted claims are in condition for payment by an insurer. A medical technician operating a client computer establishes communication with a remote server. The remote server transmits a claim form to the client computer for display to the medical technician. Using the claim form, the technician enters patient identification information, which is transmitted to the server to determine whether the patient is a beneficiary of an approved insurance plan. If the patient is a beneficiary, the technician can prepare an insurance claim using the claim form displayed by the client computer. The technician enters a diagnosis code and a treatment code representing the diagnosis and treatment of the patient. The diagnosis and treatment codes are transmitted to the remote server, which processes the codes to determine whether the claim corresponds to health care services that are approved for payment. If the insurance claim is not in condition for payment, the medical technician is notified. The medical technician can then amend the insurance claim as necessary and resubmit the claim.

12 Claims, 4 Drawing Sheets

U.S. PATENT DOCUMENTS

| | | | | |
|---|---|---|---|---|
| 5,301,105 | A | 4/1994 | Cummings, Jr. | 364/401 |
| 5,359,509 | A | 10/1994 | Little et al. | 364/401 |
| 5,519,607 | A | 5/1996 | Tawil | 364/401 |
| 5,523,942 | A | 6/1996 | Tyler et al. | 364/401 |
| 5,644,778 | A | 7/1997 | Burks et al. | 395/800 |
| 5,704,044 | A | 12/1997 | Tarter et al. | 395/204 |
| 5,903,873 | A | 5/1999 | Peterson et al. | 705/4 |
| 5,911,132 | A * | 6/1999 | Sloane | 705/3 |
| 5,915,241 | A | 6/1999 | Giannini | 705/2 |
| 5,930,759 | A | 7/1999 | Moore et al. | 705/2 |
| 6,003,007 | A * | 12/1999 | DiRienzo | 705/4 |
| 6,012,035 | A | 1/2000 | Freeman, Jr. et al. | 705/2 |
| 6,112,183 | A * | 8/2000 | Swanson et al. | 705/2 |
| 6,208,973 | B1 * | 3/2001 | Boyer et al. | 705/2 |

OTHER PUBLICATIONS

Llana, Jr. A. "Conveying the Image", Feb. 1992, v12, n8, p22(4). Gale Group Computer DB, [online] DG Review. Retrieved from: Dialog Accession No. 01513428.

"Octel unveils strategic roadmap for health care marketplace focus is on efficiency-enhancing applications global messaging" Mar. 1996, Gale Group, Retrieved from: Dialog Access. No. 01354156.

Tanner, Lisa, Claimsnet Files IPO to Fund Internet Service (The Company plans to cash in on growing market for physician's claims processing), Dallas Business Journal, May 8, 1998, vol. 21, Issue 37, p. 10 1/2p.

* cited by examiner

FIG. 1

Health Care Claims Form ⟵12a · 26 · 32

| Plan I D | |
|---|---|
| Insured's I D | |
| Paitent's date of birth | - mm/dd/yy |
| Provider I D | |

Health Care Claims Form ⟵12b

42 {
Plan ID : 1234

Insured : Doe, John 541XXXXX

Patient : 01, Jane

Provider: MISCELLANEOUS PROVIDERS
}

| Please enter the Patient Dependent Number from above from above: | | | | 48 |
|---|---|---|---|---|
| Last Name, First, Middle Initial, I.D. | | | | |
| Referring Physician | | | | |
| Service Provider | | | | |

Diagnosis or Nature of Illness or Injury.

44 · 44

| Dates of Service | | Place | Type | Procedure, Service or Supplies | | | 52 |
|---|---|---|---|---|---|---|---|
| From | To | Svc | Svc | CPT | Modifier | Diagnosis No | $Charges |
| | | | | ⟵46 | | | |
| | | | | | | | |
| | | | | | | | |
| | | | | | | | |
| | | | | | | | |
| | | | | | | | |

| Patient's Account | Accept Assign? | Total Charge | 54 |
|---|---|---|---|
| | Yes ○ No ○ | Amount Paid | 50 |
| | | Balance Due | 56 |

INTERACTIVE CREATION AND ADJUDICATION OF HEALTH CARE INSURANCE CLAIMS

1. RELATED APPLICATIONS

This application is a continuation of U.S. patent application Ser. No. 09/204,886, filed Dec. 3, 1998, now U.S. Pat. No. 6,341,265 entitled "Provider Claim Editing and Settlement System," which is incorporated herein by reference.

BACKGROUND OF THE INVENTION

1. The Field of the Invention

The present invention relates to systems for creating and approving health insurance claims. More particularly, the present invention relates to interactively creating insurance claims on a client computer that communicates with a remote server computer, whereby a health care provider can be almost immediately informed whether the created insurance claim is in condition to be paid.

2. Relevant Technology

The cost of health care continues to increase as the health care industry becomes more complex, specialized, and sophisticated. The proportion of the gross domestic product that is accounted for by health care is expected to gradually increase over the coming years as the population ages and new medical procedures become available. Over the years, the delivery of health care services has shifted from individual physicians to large managed health maintenance organizations. This shift reflects the growing number of medical, dental, and pharmaceutical specialists in a complex variety of health care options and programs. This complexity and specialization has created large administrative systems that coordinate the delivery of health care between health care providers, administrators, patients, payors, and insurers. The cost of supporting these administrative systems has increased during recent years, thereby contributing to today's costly health care system.

A significant portion of administrative costs is represented by the systems for creating, reviewing and adjudicating health care provider payment requests. Such payment requests typically include bills for procedures performed and supplies given to patients. Careful review of payment requests minimizes fraud and unintentional errors and provides consistency of payment for the same treatment. However, systems for reviewing and adjudicating payment requests also represent transaction costs which directly reduce the efficiency of the health care system. Reducing the magnitude of transaction costs involved in reviewing and adjudicating payment requests would have the effect of reducing the rate of increase of health care costs. Moreover, streamlining payment request review and adjudication would also desirably increase the portion of the health care dollar that is spent on treatment rather than administration.

Several factors contribute to the traditionally high cost of health care administration, including the review and adjudication of payment requests. First, the volume of payment requests is very high. Large health management organizations may review tens of thousands of payment requests each day and tens of millions of requests yearly. In addition, the contractual obligations between parties are complex and may change frequently. Often, there are many different contractual arrangements between different patients, insurers, and health care providers. The amount of authorized payment may vary by the service or procedure, by the particular contractual arrangement with each health care provider, by the contractual arrangements between the insurer and the patient regarding the allocation of payment for treatment, and by what is considered consistent with current medical practice.

During recent years, the process of creating, reviewing, and adjudicating payment requests from health care providers has become increasingly automated. For example, there exist claims processing systems whereby technicians at health care providers' offices electronically create and submit medical insurance claims to a central processing system. The technicians include information identifying the physician, patient, medical service, insurer, and other data with the medical insurance claim. The central processing system verifies that the physician, patient, and insurer are participants in the claims processing systems. If so, the central processing system converts the medical insurance claim into the appropriate format of the specified insurer, and the claim is then forwarded to the insurer. Upon adjudication and approval of the insurance claims, the insurer initiates a check to the provider. In effect, such systems bypass the use of the mail for delivery of insurance claims.

In partially automated systems, such as that described in the foregoing example, the technician can submit a claim via electronic mail on the Internet or by other electronic means. To do so, the technician establishes communication with an Internet service provider or another wide area network. While communication is maintained, the technician sends the insurance claim to a recipient and then either discontinues communication or performs other activities while communication is established. Using such conventional systems, personnel at the health care provider's office are unable to determine whether the submitted claim is in condition for payment and do not receive any indication, while communication is maintained, whether the claim will be paid.

Thus, while systems that permit electronic submission of insurance claims marginally decrease the time needed to receive payment by eliminating one or more days otherwise required to deliver claims by mail, they remain subject to many of the problems associated with other claims submission systems. For example, it has been found that a large number of insurance claims are submitted with information that is incomplete, incorrect, or that describes diagnoses and treatments that are not eligible for payment. The claims can be rejected for any of a large number of informalities, including clerical errors, patient ineligibility, indicia of fraud, etc. The health care provider is not made aware of the deficiencies of the submitted claims until a later date—potentially weeks afterwards—when the disposition of the insurance claim is communicated to the health care provider. As a result, many claims are subject to multiple submission and adjudication cycles, as they are successively created, rejected, and amended. Each cycle may take several weeks or more, and the resulting duplication of effort decreases the efficiency of the health care system. Studies have shown that some insurance claim submission systems reject up to 70% of claims on their first submission for including inaccurate or incorrect information or for other reasons. Many of the claims are eventually paid, but only after they have been revised in response to an initial rejection.

In order to attempt to minimize the number of claims that are rejected, physicians or their staff have had to spend inordinate amounts of time investigating which treatments will be covered by various insurers and insurance plans. The time spent in such activities represents further efficiency losses in the health care system.

Depending on a patient's insurance plan and the diagnosis and treatment rendered, the patient may be required to make a co-payment representing, for example, a certain percentage of the medical bill or a fixed dollar amount. Because of the large number of insurers and insurance plans, the amount of the co-payment can vary from patient to patient and from visit to visit. Moreover, when a patient is not covered for certain treatment, the patient may be liable for the entire amount of the health care services. It is sometimes difficult for technicians at the offices of the health care provider to determine that amount of any co-payment or any other amount due from the patient while the patient remains at the offices after a medical visit. Once the patient leaves the office, the expense of collecting amounts owed by patients increases and the likelihood of being paid decreases. Conventional insurance claim submission systems have not been capable of efficiently and immediately informing technicians at the offices of a health care provider of amounts owed by patients, particularly when the amount is not a fixed dollar amount.

In view of the foregoing, there is a need in the art for more fully automated claims processing systems. For example, it would be an advancement in the art to reduce the uncertainty as to whether a claim to be submitted is likely to be paid or rejected. Furthermore, it would be advantageous to provide a claims processing system that would more easily allow health care providers to know what patient and treatment information must accompany insurance claims. There also exists a need for systems that allow health care providers to easily learn of the status of submitted insurance claims.

SUMMARY AND OBJECTS OF THE INVENTION

The present invention relates to methods and systems for interactively creating insurance claims. According to the invention, a medical technician can prepare an insurance claim electronically, submit the claim via the Internet or another wide area network, and receive almost immediately an indication whether the submitted claim is in condition to be paid. If the medical technician is informed that the claim is not in condition to be paid, the claim can be amended by correcting errors or otherwise placing the claim in condition to be paid. By using the invention, health care providers can essentially eliminate the possibility of having claims rejected after a lengthy adjudication process. The invention can significantly reduce the time, effort, and expense that have been associated with the submission of claims that are not in condition to be paid.

According to the invention, communication is established between a client computer operated by a medical technician and a remote server computer. The communication can be established using the Internet, a direct-dial telephone line, or any other suitable wide area network infrastructure. The client computer displays a computer-displayable claim form to the medical technician. The claim form can be sent to the client computer by the remote server or can instead be retrieved from a local memory device. The claim form includes fields that permit the medical technician to enter patient identification information that identifies the patient. The patient identification information is transmitted from the client computer to the remote server. The remote server then determines whether the patient is a beneficiary of a health insurance plan and informs the client computer of the patient eligibility status.

Informing the medical technician almost immediately of the patient's insurance status allows the health care provider to select the appropriate treatment for the patient. The patient's eligibility status transmitted from the remote server can include any desired amount of detail. For example, the eligibility status can describe the types of diagnoses and treatments for which payment will be made on behalf of the patient, and the co-payment required by the patient.

If the patient is a beneficiary of an approved insurance plan, the medical technician can proceed with preparation of a full insurance claim. The claim form displayed by the client computer includes fields that permit the medical technician to enter one or more diagnosis codes describing the diagnosis of the patient and one or more treatment codes describing the treatment administered to the patient. The claim form can also include fields representing the identity of the health care provider and any other desired information.

The diagnosis and treatment codes are transmitted from the client computer to the remote server. The remote server or a processor associated therewith then processes the transmitted information to determine whether the insurance claim is in condition to be paid. For example, the remote server can verify that all required information is included. The remote server can also determine whether the diagnosis code and the treatment code correspond to currently accepted medical practice and to health care services that are covered by the particular insurance plan of the patient. The remote server can also perform any desired checks on the information in the insurance claim to determine whether the claim has indicia of fraud, unusually expensive treatment, or any other feature that indicates that the validity or accuracy of the claim should be further investigated.

If the insurance claim is not in condition to be paid, the remote server transmits information to the client computer to inform the medical technician. The information transmitted to the client computer can include an indication of the reason for rejection of the claim and, optionally, suggestions on how to remedy the problem. For instance, if the insurance claim does not include complete information, the medical technician can be prompted to complete the claim form. The deficiency of the claim can be substantive, as well, in that the treatment code could represent a treatment that is not considered to be compatible with the diagnosis. In this case, the health care provider can change the treatment, otherwise amend the claim form, or inform the patient that the insurance plan will not cover the treatment. When a claim form has been amended, the new information can be transmitted to the remote server to repeat the process of determining whether the claim is in condition to be paid.

When the remote server determines that the claim is in condition to be paid, the remote server transmits information to the client computer to notify the medical technician. The information transmitted to the client computer can include data that represents an amount that is to be paid by the insurer on behalf of the patient. The medical technician can also be informed of any co-payment to be collected from the patient. Because the process of determining whether the claim is in condition for payment can occur almost instantaneously—typically in a matter of seconds or minutes—any co-payment can be collected from the patient while the patient remains in the offices of the health care provider before or after treatment.

In view of the foregoing, the invention provides systems and methods for providing almost immediate feedback to the medical technician specifying whether a submitted claim is in condition to be paid. While the speed of response can vary, depending on the data transmission rates between the client computer and the remote server, the processing capabilities of the remote server, and the complexity of the verification process to be conducted by the remote server, the invention can provide almost immediate response to submitted claims. The response time can be short enough that the medical technician can create a claim, submit the claim, and be notified whether the claim is in condition for allowance without discontinuing communication between the client computer and the remote server, while continuing to view the claim form displayed by the client computer, or without proceeding to another patient's claim before receiving the response. In any event, the response time is significantly faster than that of conventional systems, which do not permit the interactive creation and modification of insurance claims.

The invention can significantly reduce the inefficiencies that are otherwise experienced in the health care system as claims are submitted, subjected to an adjudication process, and often rejected days, weeks, or longer, after the claim was created. The claim creation and verification systems of the invention also allow health care providers to easily learn of the types of treatments that are approved for payment for specific diagnoses according to the patient's insurance plan. In addition, the invention increases the efficiency of collecting co-payments from patients and increases the likelihood that such co-payments will be made.

Additional objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims. These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

The present invention relates to methods and systems for interactively preparing and submitting insurance claims and verifying that the claims are in condition to be paid. A medical technician at the offices of a health care provider operates a client computer that communicates with a remote server. According to one embodiment of the invention, the medical technician views a computer-displayable claim form displayed by the client computer and enters a diagnosis code and a treatment code that describe a medical diagnosis and associated treatment for a patient. The diagnosis code and the treatment code are transmitted to the remote server. The remote server performs an operation in response to the diagnosis code and the treatment code to determine if these codes correspond to health care services that are approved for payment.

If the remote server determines that the submitted claim will not be paid by an insurer, the remote server transmits information to the client computer to inform the medical technician of this result. In response, the medical technician can amend the treatment code or any other desired information on the insurance claim to place the claim in condition to be paid. After amending the claim, the claim is again submitted to the remote server, where it is again analyzed to determine whether it represents health care services that are approved for payment.

According to one embodiment, when the remote server determines that the submitted claim is in condition to be paid, the remote server transmits information to the client computer indicating the amount that is to be paid by the insurer on behalf of the patient. The system can also inform the medical technician of any co-payment to be collected from the patient.

Embodiments of the invention include or are incorporated in computer-readable media having computer-executable instructions or data structures stored thereon. Examples of computer-readable media include RAM, ROM, EEPROM, CD-ROM or other optical disk storage, magnetic disk storage or other magnetic storage devices, or any other medium capable of storing instructions or data structures and capable of being accessed by a general purpose or special purpose computer. Computer-readable media also encompasses combinations of the foregoing structures. Computer-executable instructions comprise, for example, instructions and data that cause a general purpose computer, special purpose computer, or special purpose processing device to execute a certain function or group of functions. The computer-executable instructions and associated data structures represent an example of program code means for executing the steps of the invention disclosed herein.

The invention further extends to computer systems for interactively creating and submitting insurance claims and determining whether the claims are in condition to be paid. Those skilled in the art will understand that the invention may be practiced in computing environments with many types of computer system configurations, including personal computers, multi-processor systems, network PCs, minicomputers, mainframe computers, and the like. The invention will be described herein in reference to a distributed computing environment, such as the Internet, where tasks are performed by remote processing devices that are linked through a communications network. In the distributed computing environment, computer-executable instructions and program modules for performing the features of the invention may be located in both local and remote memory storage devices.

Figure 1:
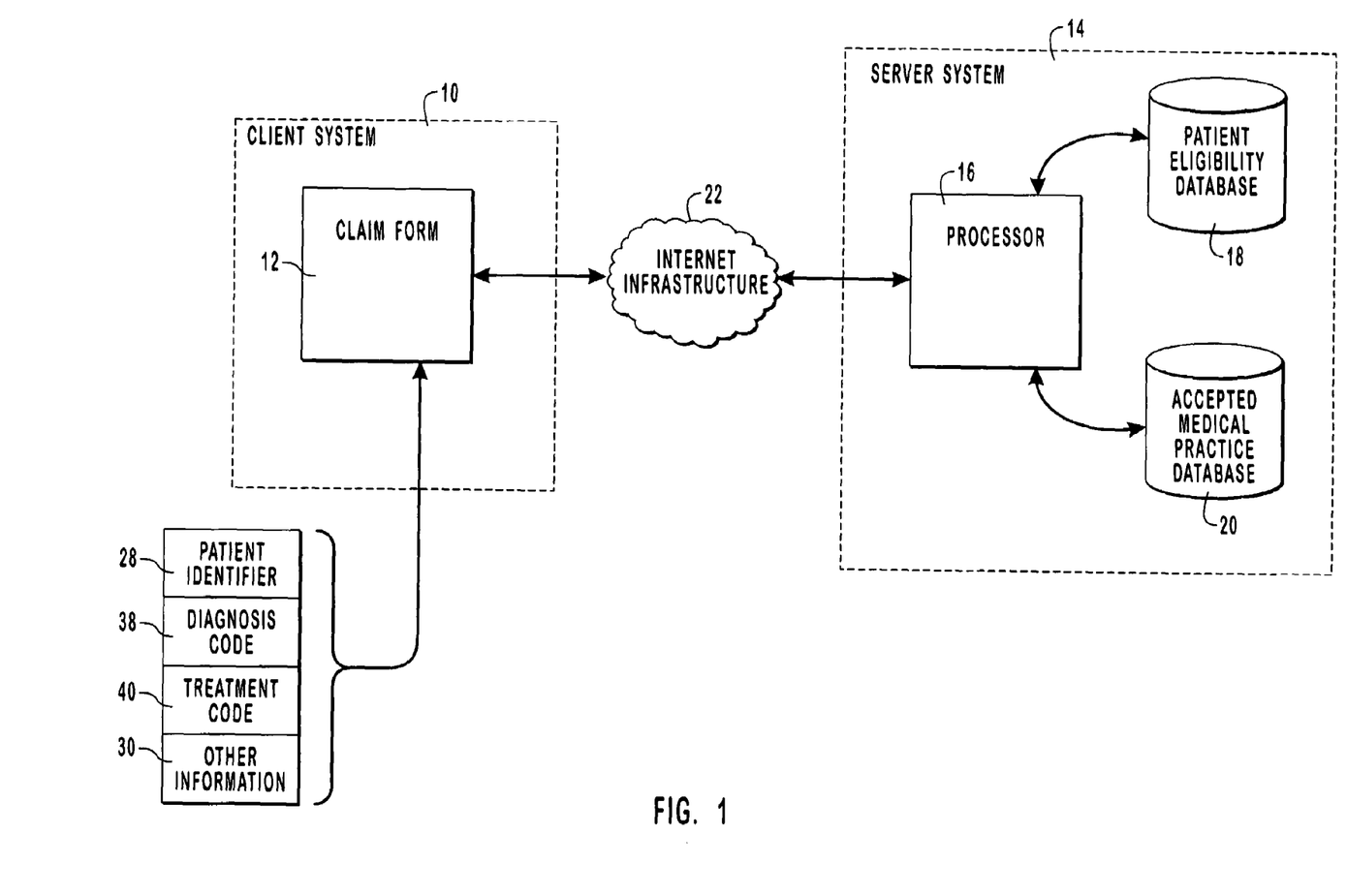
FIG. 1 is schematic diagram illustrating an interactive system according to the invention, including a client system at the offices of a health care provider and a remote server system, whereby a medical technician can interactively prepare an insurance claim that is in condition to be paid.

FIG. 1 illustrates one embodiment of the systems for interactively creating and submitting insurance claims according to the invention. Client system 10 may be located at the offices of a health care provider in order to allow a medical technician to create and submit insurance claims. As used herein, the term "health care provider" is to be broadly construed to include any physician, dentist, medical practitioner, or any other person whose services can be compensated by a health insurer, a health maintenance organization, or the like. As used herein, the term "medical technician" represents any person who engages in the activity of preparing or submitting insurance claims on behalf of a health care provider. Since medical technicians are typically employees of health care providers, representatives of health care providers, or may be the health care providers themselves, any of the claims that recite steps, operations, or procedures conducted by "health care providers" are to be construed to extend to the same steps, operations, or procedures conducted by "medical technicians", as well.

The term "insurance plan" extends to any contractual or other legal arrangement whereby medical and other related expenses are paid on behalf of a beneficiary. Examples of insurance plans include health maintenance organizations, fee-for-service health care plans, employer-sponsored insurance plans, etc.

Client system 10 can be a general purpose computer, such as a PC, or a special purpose computer adapted to perform the functions and operations disclosed herein. Client system 10 may include a display device such as a monitor for displaying claim form 12, as will be disclosed in greater detail below, and one or more input devices such as a keyboard, a mouse, etc. for enabling a medical technician to enter the required information to client system 10.

The embodiment illustrated in FIG. 1 also includes a server system 14 located typically at a remote location with respect to client system 10. Server system 14 can include a general purpose computer or a special purpose computer adapted to execute the functions and operations of the invention. For example, in FIG. 1, server system 14 includes a processor 16, which represents a general purpose computing device for receiving information associated with insurance claims and for determining whether the received information corresponds to health care services that are approved for payment. The operation of server system 14 and processor 16 will be discussed in greater detail below.

In one embodiment, processor 16 is capable of accessing information stored in a patient eligibility database 18 and an accepted medical practice database 20. Database 18 can include compilation of data that enables server system 14 to determine whether a particular patient identified at client system 10 is a beneficiary of an approved insurance plan. Likewise, database 20 can be any compilation of data that enables service system 14 to determine whether the health care services associated with a submitted claim are approved for payment under the particular insurance plan of the patient.

While the illustrated components of server system 14 of FIG. 1 can be located at a single remote site with respect to client system 10, other embodiments of the invention employ a processor 16 and databases 18 and 20 that may be located at different sites with respect to each other. The terms "server system" and "remote server" extend to the latter case, wherein the various components 16, 18, and 20 are located in a distributed environment unless specifically indicated otherwise.

In the embodiment of FIG. 1, client system 10 and server system 14 communicate by means of Internet infrastructure 22. While the invention is described herein in the context of the Internet, those skilled in the art will appreciate that other communications systems can be used, such as direct dial communication over public or private telephone lines, a dedicated wide area network, or the like.

Referring to FIG. 1, when a medical technician desires to prepare an insurance 24 claim for health care services provided to the patient, the medical technician operates client system 10 and establishes communication with server system 14 or verifies that communication has been established. For instance, the medical technician may use client system 10 to dial into a modem pool associated with an Internet service provider in Internet infrastructure 22. After communication with the Internet service provider has been achieved, client system 10 may be used to transmit a Uniform Resource Locator (URL) to the Internet infrastructure 22 that requests access to resources provided by server system 14. Alternatively, any other suitable technique can be used to establish communication between client system 10 and server system 14.

In many cases, client system 10 will maintain communication with server system 14 for an extended period of time during which claims for multiple patients are processed. For instance, client system 10 can be a dedicated terminal that maintains communication with server system 14 in order for numerous insurance claims to be created and processed.

Once communication has been established, the medical technician can use client system 10 to request claim form 12 to be displayed on a monitor associated with client system 10. Claim form 12, in one embodiment, is a Hyper Text Markup Language (HTML) document retrieved from server system 14 and displayed to the medical technician. Alternatively, claim form 12 can have any other suitable format or can be stored at a local cache or any other local data storage system, thereby eliminating the need to repeatedly retrieve claim form 12 from a remote location as multiple insurance claims are created.

Figure 2:
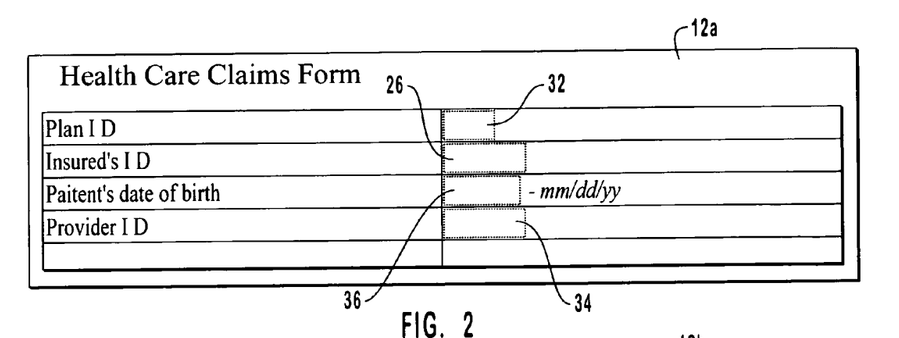
FIG. 2 illustrates an insurance claim form that enables a medical technician to determine whether and to what extent a patient is a beneficiary of an approved insurance plan.

FIG. 2 illustrates one example of a claim form 12A that enables a medical technician to verify that a patient is a beneficiary of an insurance plan and to learn of the details of the insurance plan. In this embodiment, claim form 12A includes a field 26 to which a patient identifier can be entered. Patient identification information, such as patient identifier 28 of FIG. 1, is entered by the medical technician claim form 12A of FIG. 2. Depending on the manner in which the invention is implemented, the medical technician may be required to enter other information, such as other information 30 of FIG. 1, that identifies, for example, the insurance plan of the patient, the health care provider, or the like. Turning to FIG. 2, claim form 12A in this example includes a field 32 for identifying the insurance plan of the patient, a field 34 for receiving information identifying the health care provider and a field 36 for entering additional information identifying the patient. As shown in FIG. 2, field 36 can be adapted to receive a patient's date of birth. Alternatively, any other information that can uniquely identify a particular patient from among a pool of patients can be used in combination with fields 26 and 36. By way of example and not limitation, the patient identification information entered to fields 26 or 36 can include patient's social security number, or a number uniquely associated with the patient by an insurance plan or a health maintenance organization.

Referring now to FIG. 1, after the medical technician has entered patient identifier 28 and, optionally, other information 30, the medical technician uses client system 10 to transmit the information to server system 14. In one embodiment, processor 16 compares patient identifier 28 against data stored in patient eligibility database 18 to determine if the patient is a beneficiary of an insurance plan and, if so, the details of the benefit thereof. If the patient is found not to be a beneficiary of an approved insurance plan, information is transmitted from server system 14 to client system 10 to inform the medical technician of this result. Thus, when the patient is not a beneficiary, a medical technician and the health care provider can promptly learn of this status and take steps to advise the patient or provide appropriate medical treatment.

If it is determined that the patient is a beneficiary, information is likewise transmitted from server system 14 to client system 10 informing the medical technician of the patient's status. The information can also provide details of the coverage provided to the patient that can allow the health care provider to select the appropriate course of action for the patient. The details can include the types of diagnoses and treatments that are approved for payment.

Figure 3:
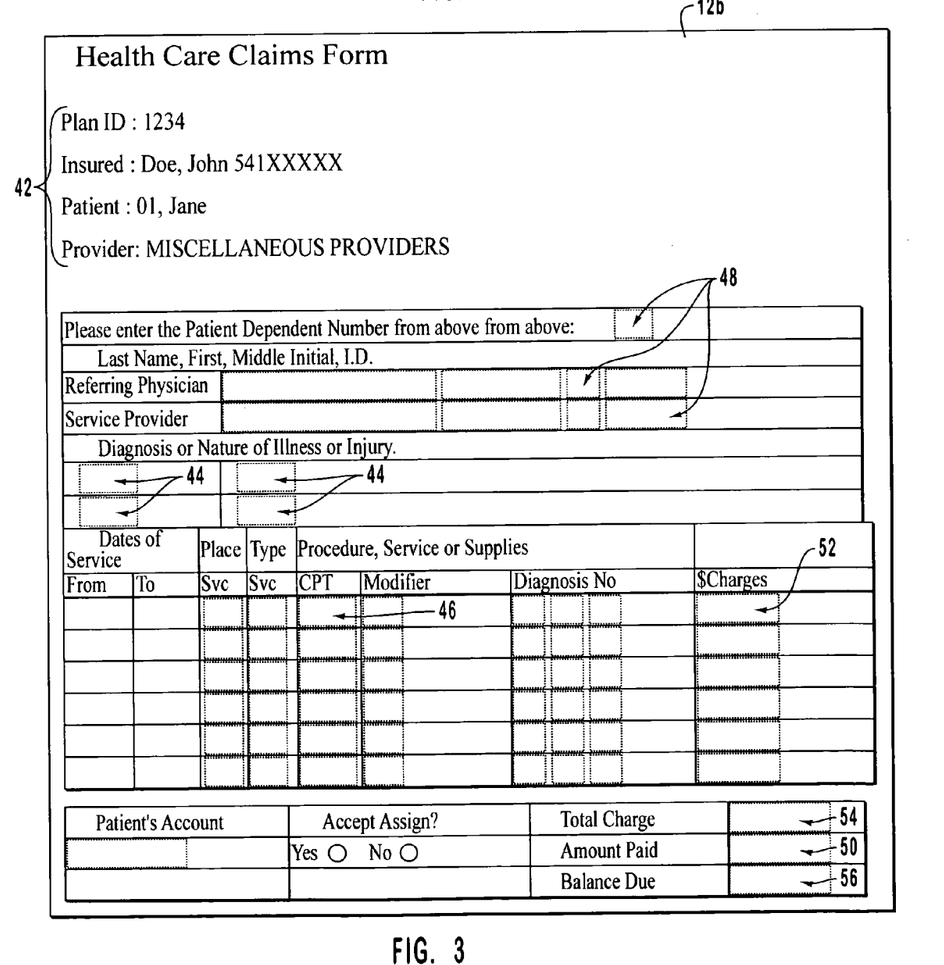
FIG. 3 illustrates an insurance claim form that enables a medical technician to submit an insurance claim including one or more diagnosis codes and one or more treatment codes.

When the health care provider makes a diagnosis and performs or prescribes treatment to the patient, the medical technician can complete the claim form by entering at least one diagnosis code 38 and one treatment code 40. Referring now to FIG. 3, claim form 12B includes fields adapted to accept the diagnosis code and the treatment code. Claim form 12B of FIG. 3 and claims form 12A may be separate forms displayed to the medical technician using client system 10 or can be separate portions of the single claim form. Claim form 12B, in the example of FIG. 3, includes header information 42 that has been automatically prepared by the server system before claim form 12B was transmitted to the client system. Providing a claim form 12B that is automatically partially completed contributes to the efficiency of the claims creation and submission processes of the invention. While claim form 12B represents a claim form that can be advantageously used by many health care providers, the specific fields included in the form and the information displayed on the form may vary from one implementation to another, depending on the type of health care provider, insurance plan, and other factors.

Claim form 12B includes a plurality of fields 44 designed to receive and display diagnosis codes representing the health care provider's diagnosis of the patient or the nature of the patient's illness or injury. Thus, as used herein, "diagnosis code" refers to any information that specifies or indicates a patient's condition as diagnosed by a health care provider. Any predefined set of diagnosis codes can be used with the invention.

Claim form 12B also includes one or more fields 46 designed to receive and display treatment codes associated with the diagnosis code of field 44. As used herein, "treatment codes" can represent any type of health care services such as clinical therapy, pharmacological therapy, therapeutic supplies or devices, or other goods or services that can be paid for by health insurance plans or health maintenance organizations. The treatment codes can be selected from any desired set of predefined treatment codes that define various treatments that can be administered to patients. In one embodiment, the diagnosis codes and the treatment codes can be selected from the codes and code modifiers of a volume entitled Physician's Current Procedural Terminology (CPT), which is maintained and updated annually by the American Medical Association.

As shown in FIG. 3, claims form 12B can include other fields, such as fields 48, that are to be completed by the medical technician before the insurance claim is submitted. In this example, fields 48 are adapted to receive and display information identifying the patient, a referring physician, and the health care provider who is to receive payment for the health care services provided to the patient.

When fields 44, 46, and 48 are filled out by the medical technician, the medical technician submits the information included in these fields to server system 14 from client system 10. Referring again to FIG. 1, server system 14 receives this information and performs certain operations in response thereto to determine whether the claim form corresponds to health care services that are approved for payment by the patient's insurance plan. For instance, processor 16 can compare the diagnosis code 38 and treatment code 40 with a compilation of currently accepted medical procedures stored in database 20. In one embodiment, MDR may be used to determine whether the diagnosis codes and treatment codes correspond to health care services that are approved for payment. Upon learning of the invention disclosed herein, those skilled in the art will understand how MDR can be used to determine whether the submitted claim form represents health care services that are approved for payment.

Server system 10 also determines whether the information provided in claim form 12B is sufficiently complete to place insurance claim in condition to be paid. For example, if the medical technician inadvertently fails to include information that identifies the referring physician, server system can detect this error and later notify client system 10 of the deficiency.

The techniques for processing submitted insurance claims at server system 14 can be as complex as desired. In one embodiment, server system 14 analyzes the information submitted using claim form 12B to determine whether there are indicia of fraud or mistake, whether unusually expensive health care services are listed in the claim, or whether manual adjudication of the insurance claim is otherwise advisable. If the claim exhibits any of the foregoing features, the claim may be forwarded to a human adjudicator for manual adjudication or may be returned to the health care provider to allow revision of the claim.

One technique that is sometimes used by health care providers to collect more money from insurance plans than is otherwise warranted is the practice of unbundling medical procedures. "Unbundling" consists of performing, for example, multiple medical procedures on a patient through a single surgical incision while submitting an insurance claim for the multiple medical procedures as if they had been performed separately. Typically, when only one incision is required to perform multiple medical procedures, the payment to the operating physician is less than the payment would be if each of the multiple medical procedures had been conducted through separate incisions. Other fraudulent unbundling techniques for submitting claims on multiple medical procedures are sometimes used as well. Thus, server system 14 can analyze the diagnosis codes and the treatment codes for indicia of unbundling practices. Furthermore, server system 14 may conduct any other checks on the submitted claim.

If server system 14 determines that insurance claims submitted using the claim forms of the invention are not in the condition to be paid for any reason, server system can transmit information to client system 10 informing the medical technician of this result. In addition, the information transmitted to the client system can indicate the basis for rejecting the insurance claim. Thus the medical technician can be informed that the claim form was not completely filled out, the treatment code is inconsistent with the diagnosis code, or any of a number of other possible reasons for rejecting the insurance claim. In response, the medical technician can amend the insurance claim by entering the correct information to the fields of claim form 12B of FIG. 3, if necessary. In other cases, the health care provider can be informed that the recommended treatment defined by treatment code 40 of FIG. 1 is not approved for payment by the patient's insurance plan. The health care provider can then advise the patient and decide to proceed with the treatment or to prescribe an alternative treatment that is approved for payment.

If the medical technician wishes to amend the insurance claim, the new information is transmitted from client system 10 to server system 14 for processing. For example, the health care provider may decide that an alternative treatment is appropriate for the patient, in which case the medical technician would enter a new treatment code to client system 10. Server system 14 then repeats the previously described process of determining whether the amended insurance claim is in condition for payment. The above-described process can be repeated as many times as desired or necessary to create and submit an insurance claim that describes health care services that are approved for payment by the patient's insurance plan.

When server system 14 informs client system 10 that a submitted claim is in a condition for payment, the server system can transmit information that specifies the amount that will be paid by the insurer on behalf of the patient. For example, claim form 12B of FIG. 3 includes a field 50 that displays a dollar amount when the server system has determined that the claim is in condition for payment. In the example of FIG. 3, fields 52 permit the medical technician to enter an amount that is requested for the treatments defined by the treatment codes in fields 46.

To illustrate, the medical technician might enter in field 46 a treatment code that represents a physical exam performed by a physician. The medical technician could then enter in field 52 a dollar amount, such as $100, that is customarily charged by the physician for a physical exam. Field 54 sums all dollar amounts entered in fields 52. In this example, if the physical exam was the only treatment rendered to the patient, field 54 would also display a dollar amount of $100. If the server system, when processing the submitted claim, determines that the patient's insurer pays only $90 for a physical exam, field 50 displays the dollar amount of $90 when the insurance claims has been processed and returned to the client system. A balance due field 56 displays the difference between the total charge field 54 and the amount paid field 50. The dollar amount displayed in field 56 represents the amount that is to be collected from the patient. As used herein, the term "co-payment" is defined to extend to the dollar amount displayed in field 56, representing the amount that is to be collected from the patient beyond the payment that is approved by the insurer.

Using the invention, medical technicians and health care providers can be informed of the status of submitted insurance claims in a relatively short amount of time that is significantly less than conventional systems, which may require days, weeks, or more. Indeed, for practical purposes, a response to the submitted insurance claim is received almost immediately by the medical technician. It can be understood that the limiting factors with respect to the speed of response include the data transmission rate supported by Internet infrastructure 22 of FIG. 1 and the other communication links between the various components of the system, the processing capabilities of processor 16 and other components of server system 14, and the complexity of the submitted claim and the nature of the claim processing techniques performed by server system 14.

In many cases, the response time is short enough that a medical technician can conveniently continue viewing the claim form associated with a particular patient at client system 10 of FIG. 1 while server system 14 performs the operations that determine whether the submitted claim is in condition to be paid. Thus, a medical technician can consecutively create and submit a series of claims and receive verification that the claims are in condition for payment. In other words, a medical technician can easily create, submit, and, if necessary, revise and resubmit, a single claim before proceeding to the next claim in a series of claims, since the response time can be very short. This is in sharp contrast to prior art systems in which the response time of days, weeks, or longer make it entirely impractical for medical technicians to complete the entire claim creation and adjudication process for one claim before proceeding to the next claim.

The systems and methods disclosed herein can be practiced in combination with the systems disclosed in co-pending U.S. patent application Ser. No. 09/118,668, entitled "Internet Claims Processing System", filed Jul. 17, 1998, which is incorporated by reference for purposes of disclosure. For example, the payment systems and payment tracking systems of the foregoing patent application can be employed with the insurance claim creation and submission techniques of the invention. Moreover, as previously described, if claims submitted to server system 14 of FIG. 1 exhibit indicia of fraud or mistake, or exceed a threshold dollar amount, the claims can be subjected to additional adjudication procedures. In one embodiment, the additional adjudication procedures can include adjudication techniques described in U.S. patent application Ser. No. 09/118,668.

The invention can be practiced with additional steps for processing or paying insurance claims or for communicating the status of submitted claims to health care providers and patients. For instance, when a claim has been submitted and approved, an explanation of benefits can be automatically created and sent to the provider, the patient, and/or to an employer of the patient. Electronic finds transfer can be used to execute payment from insurers to health care providers for approved claims.

Figure 4A:
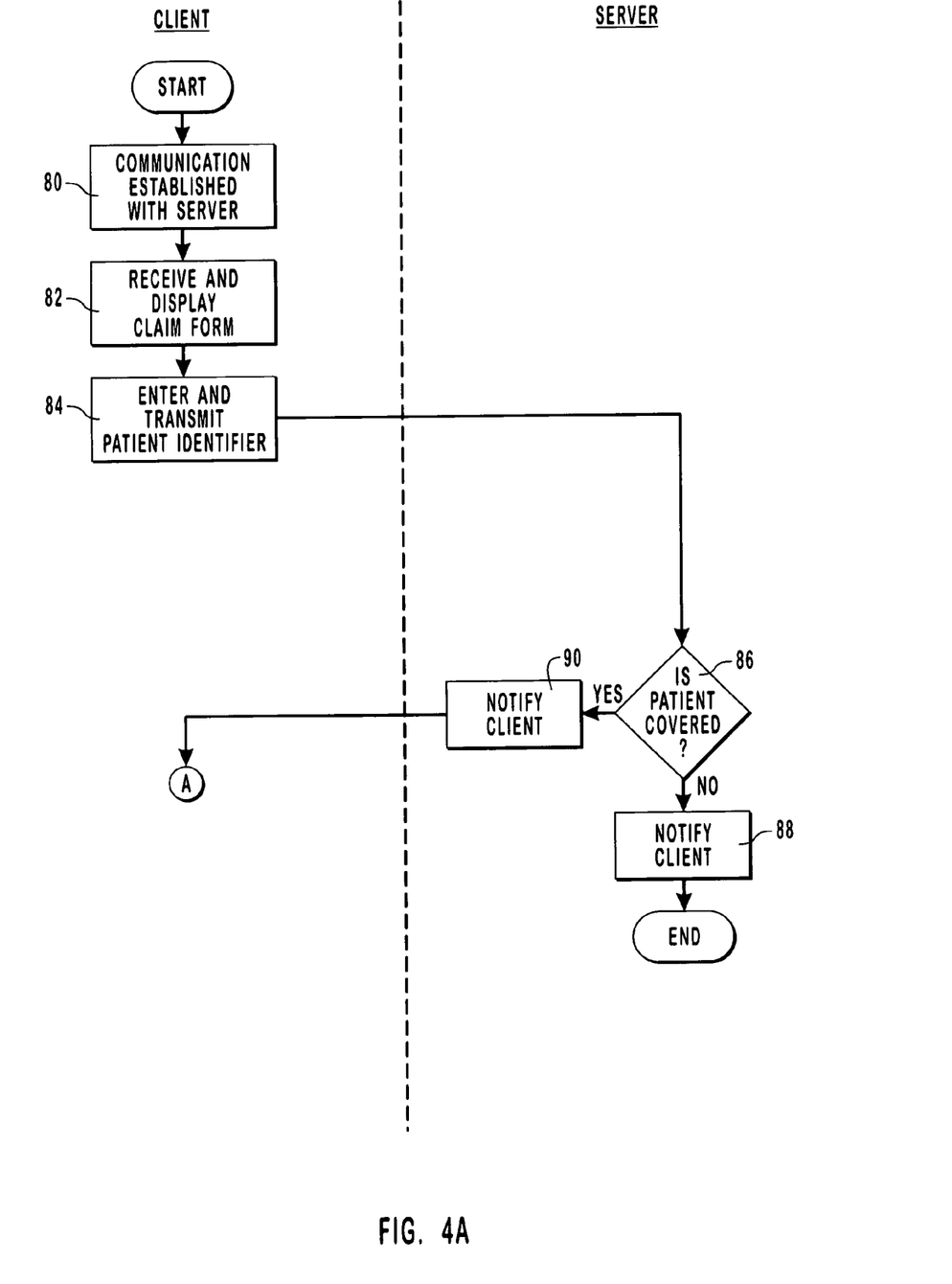
FIG. 4a is a flow diagram illustrating one embodiment of the methods of the invention for determining whether and to what extent a patient is a beneficiary of an approved insurance plan.

FIG. 4A illustrates one embodiment of the methods of the invention for interactively determining whether a particular patient is a beneficiary of an approved insurance plan. In step 80, communication is established between the client system and the server system as described herein. In step 82, the client system receives and displays the claim form to enable the medical technician to enter the information required to complete the insurance claim. As previously noted, the client system can retrieve the claim form from the remote server system or from a local data storage device. In step 84, the medical technician enters the patient identification information and transmits the information to the server system.

In decision block 86, if the server system discovers that the patient is not a beneficiary of an approved insurance plan, the server system notifies the client of this result as shown in step 88. Likewise, if the server system determines that the patient is a beneficiary, this result is transmitted to the client system as shown in step 90.

Figure 4B:
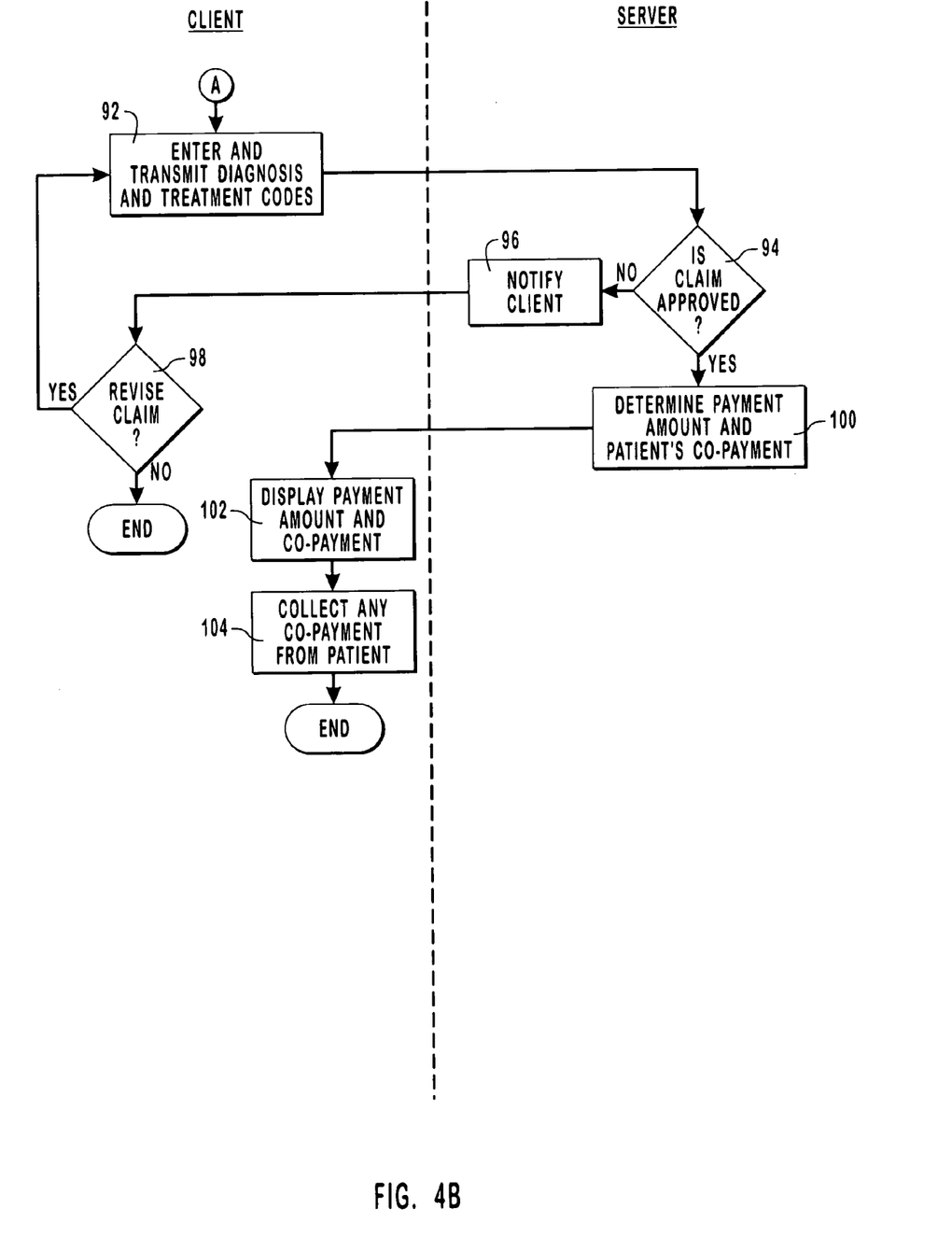
FIG. 4b is a flow diagram depicting one embodiment of the methods for interactively preparing an insurance claim that is in condition to be paid.

FIG. 4B illustrates one embodiment of the methods of the invention for creating and submitting insurance claims and determining whether the submitted claim is in condition for payment. In step 92, after having been notified that the patient is a beneficiary of an approved insurance plan, the medical technician enters the diagnosis and treatment codes to the claim form and transmits these codes to the server system. As shown in decision block 94, the server system performs any desired claim checking or adjudication process to determine whether the claim describes health care services that are approved for payment. If the claim is not in condition to be paid, the method advances to step 96, in which the client system is notified of this result. As shown by decision block 98, if the medical technician or the health care provider decides to revise the claim, the method again advances to step 92.

Referring again to decision block 94, if the server system determines that the claim is in condition for payment, the method advances to step 100, in which the server system determines the amount to be paid by the insurer and any co-payment to be collected from the patient. Next, in step 102, the client system displays the payment amount and the co-payment amount to the medical technician or the health care provider. In step 104, any co-payment can then be collected from the patient. It will also be appreciated that, in other embodiments, the invention can be practiced without calculating the co-payment.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A computer program product for implementing a method of interactively preparing an insurance claim that is in condition to be paid, the insurance claim being prepared prior to a health care provider performing health care services that are the subject of the insurance claim, wherein the method is capable of being performed on a client computer that communicates with a remote server computer, the computer program product comprising:
   a computer-readable medium carrying computer-executable instructions for implementing the method, the computer-executable instructions comprising:
      program code means for displaying a computer-displayable claim form to a health care provider;
      program code means for initiating transmission of a proposed insurance claim that includes a diagnosis code and a treatment code from the client computer to the remote server computer prior to the health care provider performing the health care services;
      program code means for receiving, from the remote server computer and prior to the health care provider performing the health care services, information indicating whether the proposed insurance claim is in condition to be paid; and
      program code means for initiating transmission of a revised proposed insurance claim, prior to the health care provider performing the health care services, if it has been determined that the proposed insurance claim is not in condition for allowance, wherein the revised proposed insurance claim includes at least one of a revised diagnosis code and a revised treatment code.

2. A computer program product as defined in claim 1, wherein the computer-executable instructions further comprise program code means for prompting the health care provider to revise at least one of the diagnosis code and the treatment code prior to the health care provider performing the health care services and in response to information received from the remote server computer indicating that the proposed insurance claim is not in condition to be paid.

3. A computer program product as defined in claim 1, wherein the program code means for initiating transmission of the proposed insurance claim comprises program code means for communicating with the remote server via the Internet.

4. A computer program product as defined in claim 3, wherein the program code means for communicating with the remote server via the Internet operate so as to maintain communication with the remote server during a time period between the transmission of the proposed insurance claim and the receipt of the information from the remote server computer.

5. A computer program product for implementing, in a server system that communicates with a client system, a method of informing a health care provider who uses the client computer whether an insurance claim represents health care services approved for payment prior to the health care provider performing the health care services, the computer program product comprising:
   a computer-readable medium carrying computer-executable instructions for implementing the method, the computer-executable instructions comprising:
      program code means for receiving a proposed insurance claim that includes a treatment code and a diagnosis code from the client computer, the treatment code and diagnosis code having been entered to the client computer by a health care provider prior to the health care provider performing health care services;
      program code means for determining whether the proposed insurance claim is in condition to be paid, including performing the act of determining whether the treatment code and the diagnosis code correspond to health care services that are approved for payment;
      program code means for initiating transmission of information to the client computer prior to the health care provider performing the health care services, the information indicating to the health care provider whether the proposed insurance claim is in condition to be paid;
      program code means for performing, if the information indicates that the proposed insurance claim is not in condition to be paid, the acts of:
         receiving a revised proposed insurance claim that includes at least one of a revised diagnosis code and a revised treatment code; and
         program code means for determining whether the revised proposed insurance claim is in condition to be paid.

6. A computer program product as defined in claim 5, wherein the computer-executable instructions further comprise program code means for initiating transmission of a computer-displayable claim form to the client computer, the claim form including fields for accepting the treatment code and the diagnosis code.

7. A computer program product as defined in claim 5, wherein the computer-executable instructions further comprise:
  program code means for receiving patient identification information from the client computer, the patient identification information identifying a patient of the health care provider;
  program code means for determining whether the patient is a beneficiary of a health insurance plan; and
  program code means for initiating transmission of data to the client computer indicating whether the patient is a beneficiary of a health insurance plan prior to the health care provider performing the health care services for the patient.

8. A computer program product as defined in claim 7, wherein the program code means for receiving patient identification information and the program code means for initiating transmission of data operate by communicating with the client computer via the Internet.

9. A computer program product as defined in claim 8, wherein the computer-executable instructions further comprise program code means for maintaining communication with the client computer during a time period between the receipt of the proposed insurance claim and the transmission of the information to the client computer.

10. A computer program product as defined in claim 5, wherein the program code means for determining whether the proposed insurance claim is in condition to be paid comprises program code means for determining that the treatment code and the diagnosis code do not correspond to health care services that are approved for payment.

11. A computer program product as defined in claim 10, wherein the computer-executable instructions further comprise program code means for:
  identifying, by the server system, the revised treatment code that, with said diagnosis code, correspond to health care services that are approved for payment; and
  prior to the health care provider performing health care services, transmitting the revised treatment code to the client computer, such that the treatment associated with the revised treatment code can be included in the health care services when the health care services are performed by the health care provider.

12. A computer program product as defined in claim 10, wherein the computer-executable instructions further comprise program code means for:
  receiving the revised treatment code from the client computer, the revised treatment code having been entered to the client computer by a health care provider;
  determining that the diagnosis code and the revised treatment code correspond to health care services that are approved for payment; and
  prior to the health care provider performing the health care services, transmitting to the client computer information indicating to the health care provider that the diagnosis code and the revised treatment code correspond to health care services that are approved for payment.

* * * * *